(12) United States Patent
Takada et al.

(10) Patent No.: US 6,890,547 B1
(45) Date of Patent: May 10, 2005

(54) GLYCYRRHIZIN PREPARATIONS FOR TRANSMUCOSAL ABSORPTION

(75) Inventors: Kanji Takada, Kyoto (JP); Masahiro Murakami, Fukuchiyama (JP)

(73) Assignee: Amato Pharmaceutical Products, Ltd., Kyoto (JP)

(*) Notice: Subject to any disclaimer, the term of this patent is extended or adjusted under 35 U.S.C. 154(b) by 400 days.

(21) Appl. No.: 10/030,058

(22) PCT Filed: Jul. 13, 2000

(86) PCT No.: PCT/JP00/04714

§ 371 (c)(1),
(2), (4) Date: Jan. 8, 2002

(87) PCT Pub. No.: WO01/05406

PCT Pub. Date: Jan. 25, 2001

(30) Foreign Application Priority Data

Jul. 16, 1999 (JP) ............................................. 11/202803

(51) Int. Cl.[7] ............................. A61F 13/02; A61F 6/06
(52) U.S. Cl. ........................ 424/434; 424/430; 424/435; 424/436
(58) Field of Search .................................. 424/430, 434, 424/435, 436

(56) References Cited

FOREIGN PATENT DOCUMENTS

| EP | 0 535 704 | | 4/1993 |
|----|-----------|---|--------|
| EP | 0535704 A | * | 4/1993 |
| JP | 3-123731 A | * | 5/1991 |
| JP | 3-123731 | | 5/1991 |
| JP | 04356424 A | * | 12/1992 |
| JP | 4-356424 | | 12/1992 |
| JP | 05139955 A | * | 6/1993 |
| JP | 5-139955 | | 6/1993 |
| WO | WO94/8622 A1 | * | 4/1994 |
| WO | 94/08622 | | 4/1994 |

* cited by examiner

*Primary Examiner*—Carlos A. Azpuru
(74) *Attorney, Agent, or Firm*—Wenderoth, Lind & Ponack, L.L.P.

(57) ABSTRACT

By blending glycyrrhizin with an ester mixture comprising a $C_{6-18}$ fatty acid glycerol ester with a $C_{6-18}$ fatty acid macrogol ester, glycyrrhizin can be efficiently absorbed via mucosae, in particular, digestive mucosae to achieve a therapeutically effective plasma glycyrrhizin concentration.

5 Claims, No Drawings

GLYCYRRHIZIN PREPARATIONS FOR TRANSMUCOSAL ABSORPTION

This application is a 371 of PCT/JP00/04714 filed Jul. 13, 2000.

TECHNICAL FIELD

The present invention relates to a glycyrrhizin preparation with improvements in absorption via mucosae, in particular digestive mucosae.

BACKGROUND ART

Glycyrrhizin is a major effective component of licorice, and is known to have many actions such as anti-allergic action, anti-inflammatory action, antiviral action and steroid-like action, and it is important as a medicine for treating chronic hepatic diseases. When glycyrrhizin is administered intravenously as an injection, the therapeutic action appears significantly. However, when it is orally administered, the therapeutic action is not clearly shown because of its poor absorption via digestive tracts.

Further, when glycyrrhizin is orally administered, it is hydrolyzed by enterobacteria present on the digestive mucosae to release its sugar moiety, and thus absorbed as glycyrrhetic acid, but the pharmaceutical activity of glycyrrhetic acid against hepatitis is considerably lower than that of glycyrrhizin.

To improve the bioavailability of glycyrrhizin, intra-rectal administration thereof in the form of suppositories has been proposed (JP-A 1-294619, JP-A 3-2122 and JP-A 3-123731).

For improving the absorption thereof via digestive tracts, an oral preparation blended with a fatty acid glyceride and coated with an enteric emulsion or a complex lipid mixture (JP-A 6-192107) have also been proposed. However, these conventional suppositories and oral preparations could not achieve blood glycyrrhizin concentrations enough to demonstrate the efficacy thereof.

Administration thereof by an injection not only gives a sharp pain to the patient but also has to be performed only by a doctor for each administration. Accordingly, administration thereof by an injection into the patient particularly having a chronic disease gives considerable mental and physical pains to the patient.

Accordingly, the object of this invention is to provide a glycyrrhizin preparation which can be administered without being performed by a doctor and giving sharp pain to humans and animals in the form of oral preparations or suppositories in place of injections.

DISCLOSURE OF INVENTION

As a result of extensive study for solving the problem described above, the present inventors found that when glycyrrhizin is dissolved or dispersed in a self-emulsifying agent comprising an ester mixture of a $C_{6-18}$ fatty acid glycerol ester with a $C_{6-18}$ fatty acid macrogol ester and then administered to digestive tracts or vagina, glycyrrhizin which has hardly achieved a sufficient blood concentration upon administration by the conventional oral preparations or suppositories can be well absorbed via digestive tracts and vaginal mucosae, particularly via colon mucosae, to achieve a blood concentration effective for treating chronic hepatic diseases, and after further extensive-study, the present invention was completed.

That is, the present invention relates to:
1. A glycyrrhizin preparation for transmucosal absorption, which comprises glycyrrhizin and an ester mixture consisting of a $C_{6-18}$ fatty acid glycerol ester and a $C_{6-18}$ fatty acid macrogol ester.
2. The glycyrrhizin preparation for transmucosal absorption according to item 1, wherein the $C_{6-18}$ fatty acid is a saturated fatty acid.
3. The glycyrrhizin preparation for transmucosal absorption according to item 1 or 2, wherein the average molecular weight of the macrogol is 100 to 800.
4. The glycyrrhizin preparation for transmucosal absorption according to item 1, wherein the ratio by weight of the glycyrrhizin to the ester mixture is 1:0.05–10.
5. The glycyrrhizin preparation for transmucosal absorption according to item 1 or 4, wherein the ratio by weight of the $C_{6-18}$ fatty acid glycerol ester to the $C_{6-18}$ fatty acid macrogol ester is 1:0.1–10.
6. The glycyrrhizin preparation for transmucosal absorption according to any one of items 1 to 5, which further comprises an organic acid, a chelating agent or a surfactant.
7. The glycyrrhizin preparation for transmucosal absorption according to any one of items 1 to 6, which is an oral preparation releasing the drug in the large intestine.
8. The glycyrrhizin preparation for transmucosal absorption according to any one of items 1 to 6, which is a rectal or vaginal suppository or a rectal or vaginal ointment.

The major component of the present invention, glycyrrhizin, is a glycoside contained in roots of licorice being a perennial plant of the pulse family, and is also called glycyrrhizic acid because it has a carboxyl group in the molecule. This glycyrrhizin also occurs in the form of salts such as alkali metal salts, and as a matter of course these salts also are included in the term of the glycyrrhizin of this invention.

Upon hydrolysis, this glycyrrhizin is converted, via a monoglucuronate derivative, into glycyrrhetic acid and two molecules of glucuronic acid, and particularly the antiviral activity of glycyrrhetic acid is regarded as being considerably lower than that of glycyrrhizin. Accordingly, it is desirable that glycyrrhizin is absorbed in the intact form into the living body in order to achieve a higher therapeutic activity.

The $C_{6-18}$ fatty acid glycerol ester comprises at least one of $C_{6-18}$ fatty acid mono-, di- and triglycerol esters, and usually a mixture thereof is used.

The $C_{6-18}$ fatty acid may be any one of saturated or unsaturated $C_{6-18}$ fatty acids, preferably saturated fatty acids and more preferably $C_{6-12}$ saturated fatty acids, that is, caproic acid, caprylic acid, capric acid and lauric acid.

In the $C_{6-18}$ fatty acid macrogol ester, the macrogol includes polyethylene glycols having usually molecular weight of 100 to 800, preferably 200 to 600, and the ester may be a mono- or diester or a mixture of mono- and diesters. The $C_{6-18}$ is fatty acid moiety constituting the macrogol ester is the same as in the above-described glycerol ester.

The mixing ratio of the glycerol ester to the macrogol ester by weight is usually 1:0.1–10, preferably 1:0.2–5.

The mixed ester consisting of the glycerol ester and macrogol ester is known as a self-emulsifying agent, and described as caprylocaproyl macrogolglycerides in the European Pharmacopoeia, and as the mixed ester, Labrasol (trade name, commercially available from Gattefosse s.a.) can be suitably used.

In this invention, the mixing ratio of the glycyrrhizin to the ester mixture by weight is usually 1 to 0.05–10, preferably 1 to 0.1–5.0.

As an absorption promoter, use can further be made of pharmaceutically acceptable organic acids such as citric acid, malic acid, maleic acid, fumaric acid and tartaric acid; pharmaceutically acceptable surfactants, for example anionic surfactants such as alkyl sulfates, nonionic surfactants such as polyoxyethylene sorbitan fatty ester, polyoxyethylene hardened castor oil, polyoxyethylene alkyl ether and polyoxyethylene alkyl phenyl ether, and steroid type surfactants such as deoxycholic acid and ursodeoxycholic acid; and chelating agents such as EDTA.

The amount of the absorption promoter used is not particularly limited, but the amount is usually 1 to 200 parts by weight, preferably about 5 to 50 parts by weight, relative to 100 parts by weight of the glycyrrhizin.

The glycyrrhizin preparation of this invention can further be mixed with an excipient, a binder, a lubricant, a swelling agent, a collapsing agent, a stabilizer, a coloring agent etc. as necessary, and formed in a method known in the art into oral preparations such as capsules, tablets, granules and powders or rectal or vaginal suppositories or rectal or vaginal ointments.

In a preferable administration form of the glycyrrhizin preparation of this invention, the major ingredient glycyrrhizin is integrated into a colon targeting drug delivery system (colon targeting DDS) designed for absorption via lower digestive mucosae.

By manufacturing glycyrrhizin into oral preparations suitable for the colon targeting drug delivery system, the administered glycyrrhizin is released at a high concentration specifically, in the large intestine, and therefore its hydrolysis by coliform bacteria is saturated, and the majority of glycyrrhizin is absorbed in the active form via the large intestine. After absorption, excretion thereof into bile is prevented due to the avoidance of the hepatic first-pass effect, and the bioavailability of glycyrrhizin itself in the active form is significantly improved.

Hereinafter, the colon targeting DDS used in this invention is described.

(1) A Method for Incorporating a Glycyrrhizin-Containing Preparation Similar to a Suppository for Rectal Administration into Capsules Made of Anionic Polymer.

The transit time of solid preparations such as capsules, tablets etc. in the small intestine is about 3 to 4 hours and relatively constant. Accordingly, the thickness of capsule wall, which is gradually dissolved within this transit time and collapsed and at the final stage to release the drug in a lower part of the small intestine, can be easily determined by an in vitro test etc.

Capsule materials suitable for this purpose include enteric acryl polymers such as Eudragid S-100 (methacrylic acid-methyl methacrylate copolymer) and Eudragid anionic polymer P4135F (methacylic acid methyl acrylate-methyl methacrylate copolymer).

As described above, it is desirable that, by collapse of capsules, glycyrrhizin is released at high concentrations in the lower digestive tracts, particularly in the large intestine, and the suitable preparation in the capsules is similar to that of a suppository for rectal administration. The method of preparing such preparations is well-known to those skilled in the art, and a suitable base material, for example Witepsol H15 (higher fatty acid di- and triglycerides, produced by Dynamit Nobel) is melted, then glycyrrhizin and other ingredients used in this invention are added thereto to produce a suspension, this suspension is filled into the above capsules, and their joints are sealed with the same polymer. Alternatively, capsules may be prepared by forming a coated layer of desired wall thickness through dipping on the surface of a preparation similar to a suppository.

(2) A Method of Enteric Coated Capsules Having Time-Controlled Release of Drug by which the Drug is Released Upon Reaching the Large Intestine (Via the Small Intestine) after Transferred from the Stomach.

The capsule produced in this method is known as CTDC (Colon Targeted Delivery Capsule) (see e.g. Takahashi: "Iyaku Journal" (Medical Journal), Vol. 34, S1, 1998, 238–242).

The pharmaceutical characteristics of CTDC is that, together with a drug, an organic acid is incorporated as a pH adjuster into conventional hard gelatin capsules, and the capsules are coated with plural layers such as a coating layer soluble in the stomach, a water-soluble coating layer and an enteric coating layer. A coated capsule preparation released in lower digestive tracts disclosed in JP-A-9-87169 also falls under this category.

(3) A Method of Using Pulsincap®

This method is described by C. G. Wilson et al. in Drug Delivery, 4:201–206 (1997). This colon delivery system makes use of a capsule consisting of a body made of an insoluble material such as low-density polyethylene and a cap made of usual gelatin. A conventional body of the capsule made of gelatin may be used after being coated with ethyl cellulose.

The body of this water-insoluble capsule is charged with excipients etc. together with the drug of this invention while a space for accommodating a stopper is left therein. Then, a stopper made of hydrogel swelling upon water absorption, for example crosslinked polyethylene glycol, is inserted via an opening into the body to seal its neck, then a gelatin cap is attached thereto, and the joint is sealed with a suitable coating solution, whereby the capsule is produced.

After the capsule is orally administered, the cap is dissolved with gastric juice, while the body of the capsule with an exposed stopper is transferred from the stomach to the small intestine. During passage through the small intestine, the stopper made of hydrogel absorbs water and gradually swells so that at a certain point in time, it is pushed out of the neck to permit the content in the capsule to be released into the digestive tract.

The time elapsed for the stopper to be pushed out of the cap of the body can be controlled by controlling of the size of the stopper.

(4) A Method of Tablets Coated with a Polymer Soluble in the Large Intestine or of Charging the Drug into Capsules Made of a Polymer Soluble in the Large Intestine.

Some bacteria in the large intestine are known to secrete an azo-reductase which reductively cleaves an azo bond. Accordingly, an azo group-containing polymer (azopolymer) is decomposed (depolymerized) specifically in the large intestine. By utilizing this phenomenon, colon targeting DDS can be designed by coating tablets with the azopolymer or by incorporating the drug into capsules made of the azopolymer.

A wide variety of azopolymers have already been known, and one example is a styrene-hydroxy ethyl methacrylate-divinyl azobenzene copolymer.

Other polymers soluble in the large intestine than the azopolymer are also known. Some examples are chitosan and one kind of polyester (CTPT polymer) having cellobiose and polytetramethylene glycol linked via an ester linkage with terephthalic acid, disclosed by the present inventors in Pharm. Tech. Japan Vol. 11 (11), 37–46 (1995).

(5) A Method of Using Time-Controlled Release Type Colon Targeting Delivery Capsules This method is disclosed as a first method in U.S. Pat. No. 5,637,319. The outline of this method lies in a system wherein capsules made of ethyl cellulose are used, and when a predetermined time is elapsed after administration, the capsules are ruptured by the pressure of a water-swelling material charged besides drug into the capsules, to release the drug.

As the swelling material, low-substituted hydroxypropyl cellulose (L-HPC), CMC sodium and CMC calcium can be used. The swelling material is molded into a mass in a shape to be fit in a capsule such as tablets, and then charged into a suitable position in the capsule, and the remaining space in the capsule is charged with a drug (glycyrrhizin in this invention) in the form of a mixture with excipients or carriers. The capsule is sealed except that the capsule wall in contact with the swelling material is provided at suitable positions with pores through which water can penetrate.

When this capsule is orally administered, the capsule is collapsed after a predetermined time by the pressure of the mass swelling gradually with water penetrating through pores, thus releasing the accommodated drug. By suitably selecting the number of pores, the diameter of pores, the thickness of the capsule wall, and the type and dimension of the swelling material, the time elapsed until the capsule is ruptured can be adjusted such that the drug is releasable in the large intestine.

(6) A Method of Using Colon Internal Pressure-Collapsing Drug Delivery Capsules

This method is described as a second method in U.S. Pat. No. 5,637,319 and also described in a journal "Preparations and Machine" on Jan. 15, 1998.

This capsule is collapsed in the large intestine according to the following mechanism. In the stomach and small intestine, ingested foods are fluidic because of abundant water in digestive juices, but in the large intestine, the viscosity of the content is significantly increased due to re-absorption of water and formation of feces. The capsule in such a high-density environment is collapsed by the internal pressure in the large intestine, resulting from peristaltic motion of the large intestine, thus permitting the drug to be released from the capsule.

This capsule is made of a high-molecular polymer such as ethyl cellulose not degraded or dissolved in digestive tracts, or a gelatin capsule lined with said polymer.

The content in the capsule is desirably a liquid upon crushing of the capsule, and accordingly the glycyrrhizin preparation, propylene glycol, polyethylene glycol, vegetable oil, and fats liquefied at the body temperature can be dissolved or dispersed in the base material and accommodated in the capsule. By changing the thickness of the ethyl cellulose-capsule wall, the collapse time of the capsule in the large intestine can be controlled.

The glycyrrhizin preparation of this invention is useful as a therapeutic and prophylactic agent against allergic diseases, abnormalities in hepatic functions in chronic hepatic diseases, various eczemas, drug rash, stomatitis, infantile strophulus, phlyctenae, alopecia areata, and viral diseases including AIDS.

The dose of the glycyrrhizin preparation of this invention may be determined in consideration of the age and weight of the patient, the type and progress of the disease, sex, administration form, administration route etc., and for treatment of hepatic diseases, about 10 to 1,000 mg, preferably 100 to 800 mg of glycyrrhizin can be administered daily into an adult (weighing 60 kg) orally all at once or in divided portions or via the rectum or vagina.

BEST MODE FOR CARRYING OUT THE INVENTION

Hereinafter, the present invention is described in more detail by reference to the Examples and Test Examples.

EXAMPLE 1

A uniform mixture of 100 mg glycyrrhizin disodium and 1.0 ml liquid consisting of water and Labrasol in a weight ratio of 1:1, per capsule, was charged into colon internal pressure controlled-release colon targeted delivery capsules lined with an ethyl cellulose film inside of the gelatin capsules, to prepare capsules for oral administration.

EXAMPLES 2 TO 4 AND COMPARATIVE EXAMPLE 1

Capsules for oral administration comprising ingredients in a compounding ratio per capsule as shown in Table 1, were produced in the same manner as in Example 1.

TABLE 1

| Ingredients | Example 1 | Example 2 | Example 3 | Example 4 | Comparative Example 1 |
| --- | --- | --- | --- | --- | --- |
| Glycyrrhizin-2 Na (mg) | 100 | 100 | 100 | 100 | 100 |
| *1 Water/Labrasol = 1/1 (ml) | 1.0 | 1.0 | 1.0 | 1.0 | |
| *2 TO-10M (ml) | | 0.05 | | | |
| Deoxycholic acid (mg) | | | 25 | | |
| *3 MYS-40 (mg) | | | | 25 | |
| EDTA-Na (mg) | | | | | 10.5 |

*1: Caprylocaproyl macrogolglycerides, produced by Gattefosse s.a.
*2: Polyoxyethylene (20) sorbitan monooleate, produced by Nikko Chemical Co., Ltd.
*2: Polyoxyethylene (40) glycol monostearate, produced by Nikko Chemical Co., Ltd.

TEST EXAMPLE 1

The glycyrrhizin-containing capsules obtained in each of Examples 1 to 4 and Comparative Example 1 were orally administered in a dose of 200 mg in terms of glycyrrhizin to each of 4 male beagles (weighing 10 to 12 kg) fasted for 12 hours from the night of the previous day. Thereafter, blood was collected with time via the carotid vein from each dog, and the plasma glycyrrhizin concentration was measured by a high-performance liquid chromatograph (HPLC). The results are shown in Table 2 (Numerical value is the average on the 4 dogs.).

TABLE 2

| | Glycyrrhizin concentration in plasma ($\mu$g/ml) | | | | | | | | |
| --- | --- | --- | --- | --- | --- | --- | --- | --- | --- |
| Time (hr) | 1 | 2 | 3 | 4 | 5 | 6 | 7 | 8 | 12 | 24 |
| Example 1 | 0 | 0 | 6 | 8 | 10 | 10 | 8 | 6 | | |
| Example 2 | 0 | 0 | 24 | 34 | 29 | 26 | 24 | 22 | | |
| Example 3 | 0 | 0 | 0 | 0.5 | 19.5 | 17 | 15 | 14 | 11.5 | 7 |
| Example 4 | 0 | 31 | 20 | 19 | 16 | 15 | 14 | 12 | | |
| Comparative Example 1 | 0 | 0 | 0 | 0 | 0.5 | 1 | 1 | 0.5 | | |

Test Results

When the preparations blended with Labrasol in Example 1 were administered, the glycyrrhizin concentration in plasma began to increase at 3 hours after administration and reached to the peak (10 $\mu$g/ml) in 5 to 6 hours to attain a therapeutic oncentration.

Any preparations comprising an absorption promoter added to Labrasol in Examples 2 to 4 achieved higher plasma concentrations than those of the preparations using Labrasol alone. On the other hand, the preparations not blended with Labrasol as in Comparative Example 1 showed no or little increase in plasma glycyrrhizin concentration.

EXAMPLE 5

A uniform mixture of 200 mg glycyrrhizin, 0.3 ml Labrasol, 0.8 ml propylene glycol and 0.1 ml Transcutol (diethylene glycol/monoethyl ether, produced by Gattefosse s.a.), per suppository, was charged into a 2 ml disposable tube for injection ointment, to produce an injection ointment.

The resultant ointment was injected into the rectum of a healthy man weighing about 60 kg, and blood was collected with time, and the plasma glycyrrhizin concentration was measured by HPLC. The results are shown in Table 3.

TABLE 3

| Time (hr) | 1 | 2 | 4 | 6 |
|---|---|---|---|---|
| Plasma concentration ($\mu$g/ml) | 2.9 | 1.8 | 0.7 | 0.1 |

As is evident from Table 3, it was confirmed that the therapeutic plasma concentration i.e. 1.0 $\mu$g/ml was achieved even by rectal administration.

EXAMPLE 6

A uniform mixture of 100 mg glycyrrhizin, 0.4 ml polyethylene glycol, 0.15 ml Labrasol, and 0.08 ml Transcutol, per capsule, where introduced into the same capsules as in Example 1, to prepare colon internal pressure collapsing colon targeted delivery capsules.

The resultant capsules were orally administered in a dose of 200 mg in terms of glycyrrhizin to the same experimental animals as in Test Example 1, and blood was collected with time, and the plasma glycyrrhizin concentration was measured by HPLC. The results are shown in Table 4 (Numerical value is the average on the 4 dogs.).

TABLE 4

| Time (hr) | 1 | 2 | 3 | 4 | 5 | 6 | 7 | 8 | 10 | 12 | 24 |
|---|---|---|---|---|---|---|---|---|---|---|---|
| Plasma glycyrrhizin concentration ($\mu$g/ml) | 6.5 | 15 | 17 | 14.5 | 15 | 15 | 14 | 12 | 13 | 12 | 9 |

INDUSTRIAL APPLICABILITY

According to this invention, glycyrrhizin which has hardly achieved a therapeutic plasma concentration by administration into digestive tracts can achieve a therapeutic plasma concentration even by oral, rectal or vaginal administration, and can achieve higher bioavailability by integrating the present preparation particularly into a colon targeting drug delivery system.

What is claimed is:

1. A glycyrrhizin oral preparation in a form of a capsule for transmucosal absorption which comprises glycyrrhizin and an ester mixture of a $C_{6-18}$ fatty acid glycerol ester with a $C_{1-18}$ fatty acid macrogol ester in a weight ratio of the glycyrrhizin to the ester mixture being 1:0.05 to 1:10, wherein the capsule is made of a high-molecular polymer which is not degraded or dissolved in a digestive tract, or which is made of gelatin lined with said polymer, and wherein the capsule is collapsed by internal pressure in a large intestine to release the glycyrrhizin.

2. The glycyrrhizin preparation for transmucosal absorption according to claim 1, wherein the $C_{6-18}$ fatty acid is a saturated fatty acid.

3. The glycyrrhizin preparation for transmucosal absorption according to claim 1, wherein the average molecular weight of the macrogol is 100 to 800.

4. The glycyrrhizin preparation for transmucosal absorption according to claim 1, wherein the ratio by weight of the $C_{6-18}$ fatty acid glycerol ester to the $C_{6-18}$ fatty acid macrogol ester is 1:0.1 to 1:10.

5. The glycyrrhizin preparation for transmucosal absorption according to claim 1, which further comprises an organic acid, a chelating agent or a surfactant.

* * * * *